(12) United States Patent
Fayerberg

(10) Patent No.: US 11,819,649 B2
(45) Date of Patent: Nov. 21, 2023

(54) NASAL INSERT AND THERAPEUTIC AGENT DELIVERY SYSTEM

(71) Applicant: Eugene Fayerberg, Ngunguru (NZ)

(72) Inventor: Eugene Fayerberg, Ngunguru (NZ)

( * ) Notice: Subject to any disclaimer, the term of this patent is extended or adjusted under 35 U.S.C. 154(b) by 317 days.

(21) Appl. No.: 17/150,312

(22) Filed: Jan. 15, 2021

(65) Prior Publication Data

US 2021/0220628 A1 Jul. 22, 2021

Related U.S. Application Data

(60) Provisional application No. 62/962,576, filed on Jan. 17, 2020.

(51) Int. Cl.
*A61M 31/00* (2006.01)

(52) U.S. Cl.
CPC ....... *A61M 31/00* (2013.01); *A61M 2205/073* (2013.01); *A61M 2210/0618* (2013.01)

(58) Field of Classification Search
CPC .......... A61M 2210/0618; A61M 31/00; A61M 2025/1075
See application file for complete search history.

(56) References Cited

U.S. PATENT DOCUMENTS

| | | | | |
|---|---|---|---|---|
| 5,011,474 A | * | 4/1991 | Brennan | A61M 27/00 606/196 |
| 2017/0224867 A1 | * | 8/2017 | Datt | A61L 24/0036 |
| 2019/0029880 A1 | * | 1/2019 | DuBois | A61F 7/03 |
| 2020/0398008 A1 | * | 12/2020 | Kemp | A61M 1/84 |

* cited by examiner

*Primary Examiner* — Deanna K Hall
(74) *Attorney, Agent, or Firm* — Sheridan Ross P.C.

(57) ABSTRACT

Methods, systems and devices for treating epistaxis are provided. In various embodiments, a nasal insert system is provided that comprises components that are operable to be at least partially inserted into a nasal cavity of a patient affected by epistaxis. Devices of the present disclosure further comprise fluid channels and conduits for selectively receiving and transmitting therapeutic agents including, but not limited to tranexamic acid.

20 Claims, 4 Drawing Sheets

NASAL INSERT AND THERAPEUTIC AGENT DELIVERY SYSTEM

This U.S. Non-Provisional Patent application claims the benefit of priority from U.S. Provisional Patent Application Ser. No. 62/962,576, filed Jan. 17, 2020, the entire disclosure of which is hereby incorporated by reference.

FIELD

The present disclosure relates to devices, systems and methods for the treating patients. In some embodiments, methods and systems of treating epistaxis are provided. More specifically, embodiments of the present disclosure relate to methods, systems and devices for treating epistaxis including a nasal insert and tranexamic acid.

BACKGROUND

Epistaxis is the clinical term for what is commonly referred to as a nosebleed. While epistaxis is common and occasionally cured by minimal intervention, it can provide a serious medical issue in situations where hemostasis is not achieved relatively quickly. Lack of hemostasis can result in the transformation of a relatively minor condition into a serious blood-loss event.

Various methods and devices are known for attempting to stop or limit epistaxis. These methods and devices include compression and application of gauze or cotton inserts. Techniques, devices, and drugs for bleeding and/or hemorrhage control are being developed, particularly for severe bleeds. However, despite all of the technology currently available, effective and prompt bleeding and hemorrhage control is still an unresolved problem in emergency medical care.

SUMMARY

There has been a long-felt and unmet need to provide methods, systems and devices for safely, quickly and effectively treating epistaxis and other conditions requiring hemostasis. Embodiments of the present disclosure provide systems, devices and methods of use comprising a nasal insert that is operable to receive an agent and that affect both a mechanical and a chemical clotting action for epistaxis. Although various embodiments of the present disclosure are well suited for and contemplated for use in the treatment of epistaxis, embodiments of the present disclosure are not so limited. It is contemplated that systems, devices and methods of the present disclosure can be employed in various situations and settings in which clotting and wound treatment are needed or desired.

In some embodiments, the present disclosure provides a device comprising a nasal insert operable to be at least partially inserted into a nostril or nasal cavity of a patient. In various embodiments, the nasal insert comprises an expandable sponge material such as polyvinyl acetal, and a porous coating or casing material at least partially surrounding the expandable sponge material. The expandable sponge material and the coating at least partially define an outer shape of the nasal insert. In some embodiments, the coating comprises a firmness, and in some embodiments comprises an antimicrobial coating and/or a lubricant. In various embodiments, a distal end of the nasal insert comprises a rounded or curved outer shape for ease of insertion into a nasal cavity.

In preferred embodiments, the coating substantially prevents or at least limits a flow of fluid (e.g., blood) from the patient to the expandable sponge material provided within the coating. The coating also allows for egress of material (e.g., tranexamic acid or "TXA") from the interior of the device and the sponge material through the coating such that TXA can be transmitted to a patient's nasal cavity and/or other tissues to enhance clotting in a patient. In various embodiments, this egress and flow of TXA (for example) is accomplished by the provision of a desired porosity in the coating and/or a positive pressure within the device. Various known devices provide nasal plugs comprising a fibrous, absorbent material that expands in response to an absorption of fluid and provide an outward force for contacting a patient. While such features and functionality are contemplated for use with embodiments of the present disclosure, preferred embodiments of the present disclosure provide for an absorbent sponge member that is bound or at least partially constrained within a coating. Alternative embodiments, however, contemplate that an insertable portion of the device can expand due to absorption of blood and/or injection of TXA or other therapeutic agent(s).

In various embodiments, nasal inserts are provided that comprises a length of between approximately 2.0 cm and 10.0 cm, and more preferably of between about 4.5 cm and 6.5 cm. In various embodiments, the nasal insert comprises a width of between approximately 1.0 cm and 5.0 cm, and more preferably of between about 1 cm and 2 cm.

In preferred embodiments, the nasal insert comprises an internal channel or conduit for fluid transport. In some embodiments, the internal channel comprises at least one porous tubing member or channel that is operable to deliver and distribute a therapeutic agent to at least a portion of the nasal insert. In preferred embodiments, the internal channel comprises a porous tubing member having an inner diameter of between about 1 mm and 5 mm and preferably of about 3 mm. The internal channel is operable to receive, transmit, and distribute fluid in various embodiments. In some embodiments, the internal channel is in fluid communication with a second channel that extends from the nasal insert and wherein the second channel is operable to receive fluids and agents (for example, from a user-operable syringe or other external source). The second conduit is contemplated as comprising a co-formed extension of the internal channel, but it is also contemplated that the second conduit comprises an additional component that is connected to the internal channel (e.g., by a threaded connection). In alternative embodiments, at least one end of the device comprises a port or aperture to receive a conduit or syringe for the direct injection of fluid (e.g. TXA) into an internal volume of the device (e.g. an internal channel and/or a porous material provided within the device).

In preferred embodiments, the nasal insert is operable to receive a drug or therapeutic agent including, for example, tranexamic acid ("TXA"). In some embodiments, devices are operable to receive a known syringe housing TXA and wherein the contents of the syringe are operable to be injected and transmitted to the nasal insert and ultimately a patient. In preferred embodiments, the contents of the syringe are allowed to at least partially saturate the internal sponge material of the insert, and the coating that at least partially surrounds the sponge is porous such that egress of TXA from the sponge is enabled. Devices and methods of the present disclosure thus provide for treatment of epistaxis by providing direct pressure to a patient's tissue and by providing activation of blood clotting with mechanical means (e.g. sponge) and simultaneously applying TXA to an affected site.

In various embodiments of the present disclosure, methods of treating epistaxis are provided. In one embodiment, a method of treating epistaxis is provided that comprises providing a nasal insert having an internal conduit, at least partially inserting the nasal insert into a nasal cavity, placing a pre-filled container in fluid communication with the internal conduit, injecting the contents of the pre-filled container into the internal conduit, allowing the contents of the syringe to be distributed within the nasal insert, removing the pre-filled syringe, and allowing the insert to remain in the nasal cavity for a period of time.

In some embodiments, a nasal insert is provided that comprises an integrated, pre-filled chamber housing a therapeutic agent. For example, in some embodiments, a pre-filled container having TXA is provided, and a seal is provided. The seal comprises a removable or breakable seal that can be broken to quickly place the nasal insert in fluid communication with the contents of the pre-filled container and thereby avoid the need to fill and/or connect a syringe with TXA to components of the nasal insert.

Various embodiments contemplate devices and methods wherein a therapeutic agent (e.g. TXA) is applied to and/or transmitted through a device during use and treatment. In certain embodiments, it is contemplated that devices of the present disclosure are pre-loaded or pre-treated with a therapeutic agent. In certain embodiments, for example, it is contemplated that devices of the present disclosure are provided with a therapeutic agent within an internal volume of the device and the device(s) are packaged or otherwise stored under positive pressure relative to atmospheric pressure to prevent premature or unwanted egress of the therapeutic agent from the device. Upon opening or activating the device and packaging (preferably just prior to insertion into a nasal cavity, for example), the device(s) experience a drop in pressure and the therapeutic agent is allowed to flow from or otherwise escape the internal portions of the device.

In one embodiment, a nasal insert for treating epistaxis is provided that comprises an expandable foam member at least partially surrounded by and connected to an outer member, wherein the foam member and the outer member are sized and operable to be at least partially inserted into a human nasal cavity. The foam member comprises a proximal end, a distal end and a length extending therebetween. An internal channel is provided within the foam member and extends along at least a portion of the length. An external conduit is provided in fluid communication with the internal channel, and wherein the external conduit comprises a proximal end and a distal end. In some embodiments, the external conduit comprises a one-way valve.

In one embodiment, a method of treating epistaxis is provided that is comprised of a nasal insert having an expandable foam member at least partially surrounded by and connected to an outer member. In preferred embodiments, the foam member and the outer member are sized and operable to be at least partially inserted into a human nasal cavity. In alternative embodiments, the foam member and the outer member are sized to fit at least partially within other cavities and/or be applied to various wounds. An internal channel provided within the foam member and extends along at least a portion of the length, and an external conduit is provided in fluid communication with the internal channel. At least a portion of the nasal insert is inserted into a nasal cavity of a patient. A container comprising tranexamic acid is provided and is placed in communication with the external conduit. The contents of the container are dispensed into the expandable foam member by conveying the contents through the external conduit and the internal channel. The container is detached from the external conduit and the nasal insert with tranexamic acid is allowed to rest within the nasal cavity for a predetermined amount of time. In some embodiments, the step of dispensing comprises activating a plunger rod of the container. In some embodiments, the predetermined amount of time comprises at least 15 seconds.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In addition, the materials, methods, and examples are illustrative only and are not intended to be necessarily limiting.

DETAILED DESCRIPTION

Figure 1:
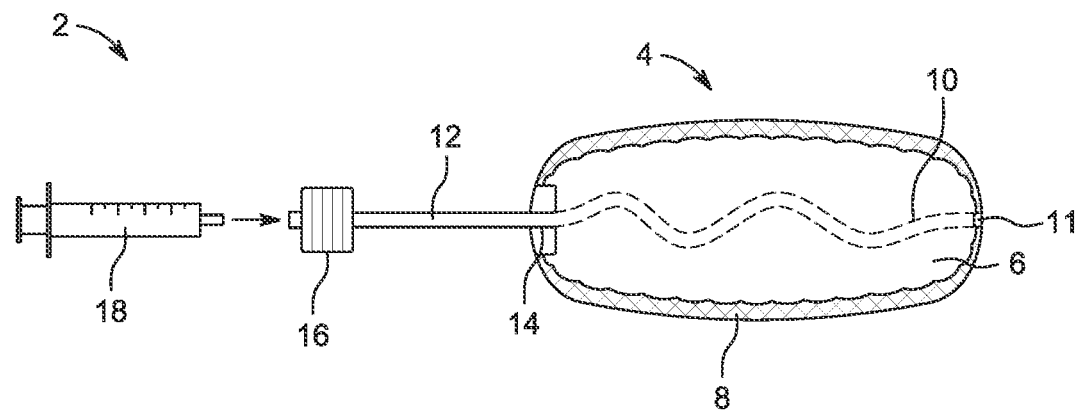
FIG. 1 is an elevation view of a system according to one embodiment of the present disclosure.

FIG. 1 is an elevation view of a treatment device according to one embodiment of the present disclosure. As shown, a system 2 is provided that comprises a nasal insert 4. The nasal insert 4 comprises an expandable member 6 with a rounded or curved shape at least at its distal end. The expandable member 6 is at least partially surrounded by an outer member 8. The outer member 8 is contemplated as comprising a coating having different material properties than the expandable member 6. The outer member is contemplated as comprising a lubricated coating in various embodiments. In some embodiments, the outer member 8 comprises an antimicrobial lubricant.

An internal channel or conduit 10 is provided for transmitting fluids. In the depicted embodiment, the internal channel 10 comprises a curvilinear shape or path to increase surface area contact between the channel 10 and the expandable member 6. It should be recognized, however, that the present disclosure is not limited to internal channels having the shape shown in FIG. 1. It is contemplated, for example, that the internal channel 10 comprises a straight or corkscrew shape in alternative embodiments.

As shown in FIG. 1, an external conduit 12 is provided that is in fluid communication with at least the internal channel 10. In preferred embodiments, the external conduit 12 comprises a flexible tubing member (e.g. plastic) that extends from the nasal insert and provides a connection and insertion point for therapeutic agents including but not limited to TXA. The external conduit 12 is also contemplated as providing a means for holding, manipulating, inserting, and removing the nasal insert into a nasal cavity. The external conduit 12 comprises a distal end that connects or transitions to the internal channel 10 and a proximal end. In various embodiments, the proximal end comprises a port 16 and a connection operable to receive a container including, for example, a syringe for injecting a therapeutic agent. In some embodiments, the port 16 comprises a one-way valve or a check valve to allow fluid(s) to be injected into the external conduit 12 and the internal channel 10 and prevent backflow of the fluid(s). The external conduit comprises a length of between approximately 1.0 and 5.0 cm, and preferably of about 3.0 cm.

Although various embodiments of the present disclosure contemplate and are depicted as comprising an external conduit and an internal channel, the present disclosure is not limited to embodiments comprising these features. For example, in some embodiments, it is contemplated that a nasal insert is provided that does not comprise an external conduit. In such embodiments, an end of the device is contemplated as comprising a port or receiving portion for a tube, syringe, or similar device that is operable to receive, inject, and/or transfer material (e.g. TXA) into the device. Additionally, alternative embodiments of the present disclosure are contemplated as comprising devices that do not have an internal channel. For example, it is contemplated that an interior of a device(s) comprises a porous inner member that does not comprise a single conduit for fluid. Such devices may be provided with or without external conduits as shown and described herein.

As shown in FIG. 1, an annular sealing element 14 is provided. The sealing element 14 comprises an anchor point wherein the outer member 8 is secured to the expandable member 6. In some embodiments, the outer member 8 comprises a mesh or permeable wrap that extends at least partially around an outer portion of the expandable member 6 and is connected at the sealing element 14. In various embodiments, at least one of the outer member 8 and the expandable member 6 is heat sealed to the sealing element 14. In preferred embodiments, the internal channel 10 comprise a sealed distal end 11 wherein fluid flow from the distal end 11 is prevented and fluid (e.g., TXA) is allowed to exit the internal channel 10 via perforations in the sidewall of the internal channel 10.

Figure 2:
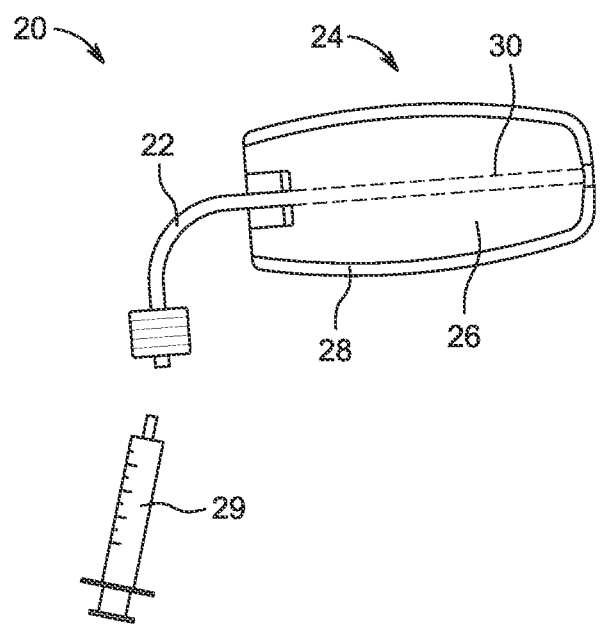
FIG. 2 is an elevation view of a system according to another embodiment of the present disclosure.

FIG. 2 is an elevation view of a treatment device according to another embodiment of the present disclosure. As shown, the device 20 comprises a nasal insert 24. The nasal insert 24 comprises an expandable sponge member 26 with a rounded or curved shape at least at its distal end. The expandable member 26 is at least partially surrounded by an outer member 28. The outer member 28 is contemplated as comprising a coating having different material properties than the expandable member 26. The outer member is contemplated as comprising a lubricated coating in various embodiments. In some embodiments, the outer member 8 comprises an antimicrobial lubricant.

Various embodiments of the present disclosure, including that shown in FIG. 2, provide an outer member 28 that is coated or otherwise treated with TXA and it is contemplated that the TXA is activated at least in part by a second agent including, for example, normal saline. In the depicted embodiment, a delivery container 29 is provided that comprises normal saline. The saline is contemplated as being injected through a delivery channel 22 and is transmitted to the outer member 28 by the expandable member 26.

Figure 3:
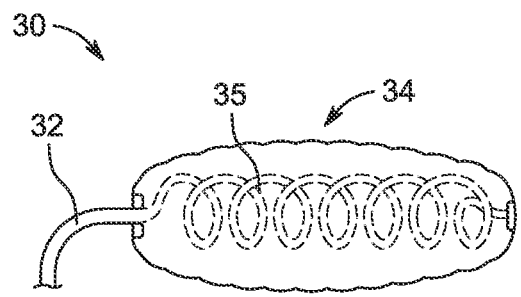
FIG. 3 is an elevation view of a system according to another embodiment of the present disclosure.
Figure 4:
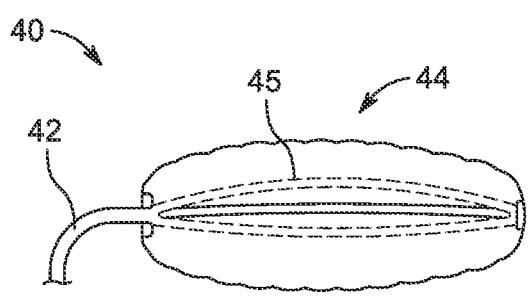
FIG. 4 is an elevation view of a system according to another embodiment of the present disclosure.
Figure 5:
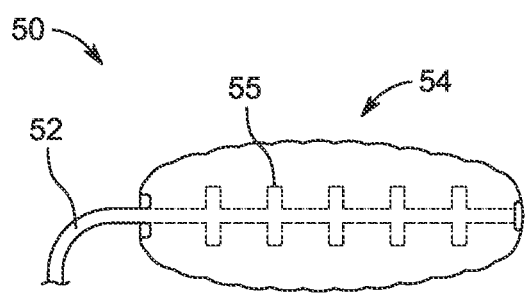
FIG. 5 is an elevation view of a system according to another embodiment of the present disclosure.

FIGS. 3-5 are elevation view of treatment devices according to alternative embodiments of the present disclosure. The devices 30, 40, 50 of FIGS. 3-5 comprise devices that are similar in function to that shown and described in FIG. 1. FIGS. 3-5, however, illustrate internal channels 35, 45, 55 of alternative embodiments of the present disclosure. FIG. 3 shows a helical or coiled arrangement to the internal channel 35. FIG. 4 illustrates an internal channel 45 comprising a series of parallel tubes. FIG. 5 shows an internal channel 55 comprising a series of branches. Accordingly, it should be recognized that various different shapes and structures for the internal channel(s) of the present disclosure are contemplated.

Figure 6:
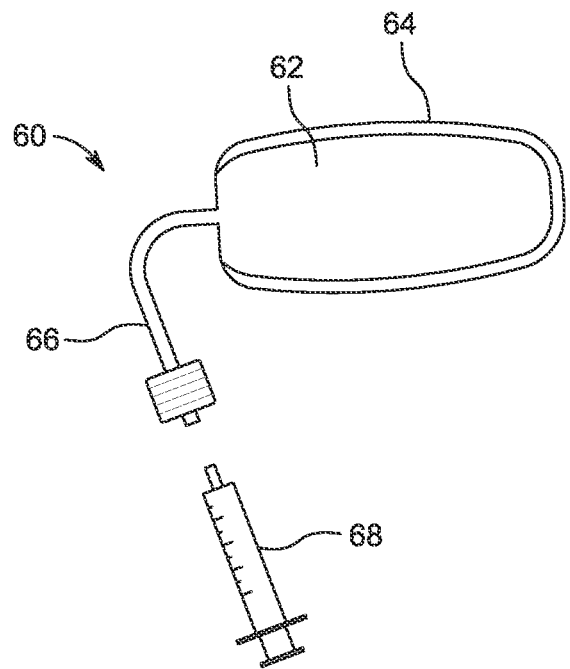
FIG. 6 is an elevation view of a system according to another embodiment of the present disclosure.

FIG. 6 is an elevation view of yet another embodiment of the present disclosure. As shown, a treatment device 60 is provided that comprises a bladder 62 within a lining or housing 64. The lining 64 preferably comprises an expandable member that is coated or treated with TXA. The bladder 62 comprises an elastic expandable member that is operable to receive at least one of fluid and pressure to expand the bladder 62 and the housing 64. In some embodiments, the bladder 62 comprises a conduit 66 for delivering fluid (e.g., air). A delivery device 68 (e.g. syringe) is provided for delivering fluid to the conduit 66 and the bladder 62. The lining 64 is operable to be forced against and/or provided in compression with a patient. The device may be inserted into a nasal cavity, for example, and fluid or pressure can be applied to expand the TXA-containing portions of the device to an affected area.

Figure 7:
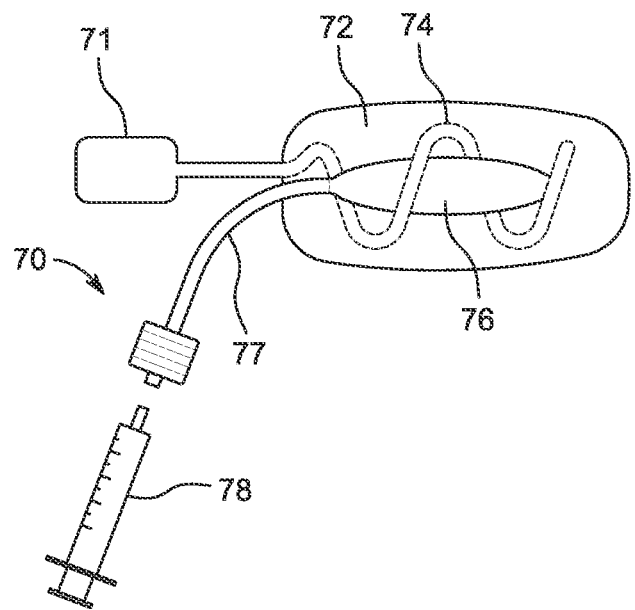
FIG. 7 is an elevation view of a system according to another embodiment of the present disclosure.

FIG. 7 is an elevation view of yet another embodiment of the present disclosure. As shown, the embodiment of FIG. 7 provides a device 70 comprising a TXA delivery mechanism and an expansion mechanism. The device 70 comprises a pre-filled container 71 for housing TXA or other therapeutic agents. The container 71 is in fluid communication with an internal conduit 74 that extends at least partially into an expandable member 72 and wherein the contents of the container 71 are operable to be provided to and expelled into the expandable member 72. In use, the expandable member is contemplated as being provided within a nasal cavity of a patient. A bladder 76 is provided within the expandable member 72. In some embodiments, including that depicted in FIG. 7, the internal conduit 74 extends at least partially around the bladder 76. The bladder is in fluid communication with a conduit 77 and a delivery device 78 that are operable to provided at least one of fluid and pressure to the bladder 76. During use, a therapeutic agent such as TXA is contemplated as being expelled from the container. To effectuate and increase delivery of the agent to a patient, fluid and/or pressure is provided from the delivery device 78 to expand at least one of the internal conduit 74 and the expandable member 72. The device of FIG. 7 provides for the delivery of a therapeutic agent and compression to a treatment area (e.g., nasal cavity).

Figure 8:
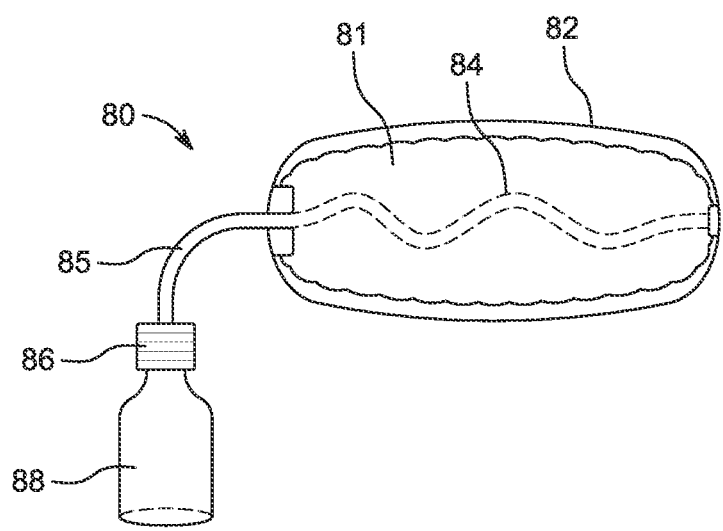
FIG. 8 is an elevation view of a system according to another embodiment of the present disclosure.

FIG. 8 is an elevation view of yet another embodiment of the present disclosure. As shown, the device 80 comprises an insertable device having an expandable sponge member 81 with an outer coating member 82. A conduit 84 extends at least partially through the sponge member 81. The conduit 84 is preferably porous or permeable to allow for one or more therapeutic agents to be provided to the sponge member 81 and/or the outer coating 82. The conduit 84 is in fluid communication with a delivery channel 85 and a container 88. The container 88 is contemplated as comprising a pre-filled compressible container for housing a therapeutic agent (e.g. TXA). The compressible container may comprise a plastic, silicone, or similar material. The container 88 preferably comprises a breakable seal 86 that is operable to be broken or opened just prior to use. The device of FIG. 8 is contemplated as comprising a pre-filled, self-contained and ready to use device for quickly administering treatment to a patient affected by epistaxis. In use, the nasal insert is at least partially inserted into a patient's nasal cavity. The seal 86 is broken open, and manual compression is used to expel contents of the container from the container 88 to the insertable portion. The entire device 80 may be allowed to rest or remain in the nasal cavity until treatment is deemed to be complete.

It is to be understood that the disclosure is not limited to particular methods or systems, which can, of course, vary. It is also to be understood that the terminology used herein is for the purpose of describing particular embodiments only and is not intended to be limiting.

A number of embodiments of the disclosure have been described. Nevertheless, it will be understood that various modifications may be made without departing from the spirit and scope of the present disclosure. Accordingly, other embodiments are within the scope of the following claims.

What is claimed is:

1. A nasal insert for treating epistaxis, the insert comprising:
    an expandable inner member at least partially surrounded by an outer coating, wherein the expandable inner member and the outer coating are sized and operable to be at least partially inserted into a human nasal cavity;
    wherein the outer coating is operable to limit a flow of fluid from the patient to the expandable inner member and permits egress of material from the expandable inner member;
    wherein the expandable inner member comprises a proximal end, a distal end and a length extending therebetween;
    an internal channel provided within the expandable inner member and extending along at least a portion of the length;
    an external conduit in fluid communication with the internal channel, and wherein the external conduit comprises a proximal end and a distal end; and
    wherein the external conduit comprises a fluid flow path and is operable to provide a contact point for a user to hold, manipulate, insert, and/or remove the insert from the human nasal cavity.

2. The nasal insert of claim 1, wherein the outer coating comprises porous cellulose.

3. The nasal insert of claim 1, wherein the outer coating is operable to limit blood flow to the expandable inner member and the inner member is operable to receive and deliver a therapeutic agent.

4. The nasal inset of claim 3, wherein the expandable inner member comprises polyvinyl acetate.

5. The nasal insert of claim 1, wherein the internal channel comprises a porous channel.

6. The nasal insert of claim 1, wherein the expandable inner member comprises tranexamic acid.

7. The nasal insert of claim 1, wherein the proximal end of the external conduit comprises a threaded connector for selectively receiving a syringe.

8. The nasal insert of claim 1, wherein a length of the external conduit comprises a length of not more than approximately 8 centimeters.

9. A nasal insert for treating epistaxis, the insert comprising:
    an inner member at least partially surrounded by and connected to an outer coating, wherein the inner member and the outer coating are sized and operable to be at least partially inserted into a human nasal cavity;
    wherein the outer coating is operable to limit a flow of fluid from the patient to the inner member and permits egress of a therapeutic agent from the inner member;
    wherein the inner member comprises a proximal end, a distal end and a length extending therebetween;
    an external conduit in fluid communication with the inner member, and wherein the external conduit comprises a proximal end and a distal end; and
    wherein the external conduit comprises a fluid flow path that is operable to convey the therapeutic agent to the inner member.

10. The nasal insert of claim 9, wherein the outer coating comprises porous cellulose.

11. The nasal insert of claim 9, wherein the inner member is expandable.

12. The nasal inset of claim 9, further comprising an internal conduit extending in the inner member and wherein the internal conduit is in fluid communication with the external conduit.

13. The nasal insert of claim 12, wherein the internal channel comprises a porous channel.

14. The nasal insert of claim 9, wherein the proximal end of the external conduit comprises a threaded connector for selectively receiving a syringe.

15. A nasal insert for treating epistaxis, the insert comprising:
    an inner member at least partially surrounded by and connected to an outer coating member, wherein the inner member and the outer coating member are sized and operable to be at least partially inserted into a human nasal cavity;
    wherein the outer coating member is operable to limit a flow of fluid from the patient to the inner member and permits egress of a therapeutic agent from the inner member;
    wherein the inner member comprises a proximal end, a distal end and a length extending therebetween;
    an internal channel provided within the inner member and extending along at least a portion of the length;
    wherein the internal channel comprises a fluid flow path and is operable to convey and dispense a therapeutic agent.

16. The nasal insert of claim 15, wherein the inner member is expandable and comprises polyvinyl acetate.

17. The nasal insert of claim 15, wherein the internal channel comprises a porous channel having pores along its length.

18. The nasal insert of claim 15, further comprising an external conduit in fluid communication with the internal channel.

19. The nasal insert of claim 18, wherein a proximal end of the external conduit comprises a threaded connector for selectively receiving a syringe.

20. The nasal insert of claim 15, wherein a length of the external conduit comprises a length of not more than approximately 8 centimeters.

* * * * *